United States Patent [19]

Jayaratna

[11] Patent Number: 5,547,553
[45] Date of Patent: Aug. 20, 1996

[54] MERCURY THREAD ELECTRODE

[75] Inventor: Husantha G. Jayaratna, Tippecanoe County, Ind.

[73] Assignee: Bioanalytical Systems, Inc., W. Lafayette, Ind.

[21] Appl. No.: 426,358

[22] Filed: Apr. 21, 1995

[51] Int. Cl.$^6$ .................................................. G01N 27/26
[52] U.S. Cl. .......................... 204/413; 204/412; 204/415; 204/409; 436/73; 436/74; 436/75; 436/52; 436/53
[58] Field of Search .................................. 204/412, 415, 204/413, 409; 436/73, 74, 75, 52, 53

[56] References Cited

U.S. PATENT DOCUMENTS

| | | | |
|---|---|---|---|
| 4,548,679 | 10/1985 | Guidelli et al. | 204/413 |
| 4,563,249 | 1/1986 | Hale | 204/415 |
| 4,661,210 | 4/1987 | Tenval | 204/413 |
| 4,804,443 | 2/1989 | Newman et al. | 204/413 |
| 4,845,517 | 7/1989 | Temple et al. | 346/140 R |
| 4,846,955 | 7/1989 | Osteryoung et al. | 204/413 |
| 5,131,999 | 7/1992 | Gunasingham | 204/413 |
| 5,292,423 | 3/1994 | Wang | 204/413 |
| 5,326,451 | 7/1994 | Ekechukwu | 204/413 |
| 5,378,343 | 1/1995 | Kounaves et al. | 204/413 |

OTHER PUBLICATIONS

Peters & Howell, A Controlled Growth Mercury Electrode, Current Separations, Jun. 1994.

Jayaratna, Mercury Thread Electrode Modified with a Hydrophilic Dialysis Polymer, Analytical Chemistry, vol. 66, No. 18, Sep. 15, 1994, pp. 2985–2988.

Bowers & Wilson, Voltammetric Membrane Electrodes. I. Basic Theory and Characteristics of Thallous and Cadmium Reduction, J. Anal. Chem, vol. 80, 1978, pp. 2968–2972.*

Pungor, Nagy & Feher, The Flat Surfaced Membrane Coated Mercury Electrode as Analytical Tool in Voltammetric Analysis, J. Electroanal. Chem., vol. 75, 1977, pp. 241–254.*

Stewart & Smart, Differential Pulse Anodic Stripping Voltammetry of Cadmium (II) with a Rotating Membrane–Covered Mercury Film Electrode, Anal. Chem. vol. 56, 1984, pp. 1131–1135.*

*Primary Examiner*—Bruce F. Bell
*Attorney, Agent, or Firm*—Ice Miller Donadio & Ryan; Doreen J. Gridley

[57] ABSTRACT

An improved mercury electrode for electrochemical analysis is formed by a small diameter thread of liquid mercury contained within an inert tube which, at one point along its length, has an short, fixed length of thin walled tubular semipermeable membrane surrounding and forming the electrodes' active surface in order to prevent or reduce fouling of the surface while allowing the mercury thread to be advanced through the membrane to expose a fresh active surface whenever desired.

10 Claims, 3 Drawing Sheets

MERCURY THREAD ELECTRODE

FIELD OF THE INVENTION

This present invention relates generally to chemical apparatus and more specifically to a liquid mercury electrode contained within a semipermeable membrane for electrolytically analyzing or testing solutions of interest by, for example, voltammetry.

BACKGROUND OF THE INVENTION

Voltammetry is a group of techniques involving very accurate measurements of current flow as a function of potential (voltage) over a period of time. Usually the potential of the working electrode is controlled to precisely known values (which may vary in a controlled manner as a function of time) with respect to a reference electrode placed in a solution to be analyzed. Any electroactive substance in the solution will transfer electrons to (anodic oxidation), or accept electrons from (cathodic reduction), the external circuit at the active surface of the working electrode whenever the potential is in a characteristic range. The magnitude of the current is proportional to the concentration of the substance in solution and the characteristic potential depends on the identity of the substance; thus voltammetry can be used for both quantitative and qualitative electrochemical analysis.

Voltammetry is often carried out with a three-electrode configuration in an electrochemical cell containing electrolyte solutions, which may be purely aqueous, nonaqueous or mixtures of water and a solvent. A potentiostat is employed to accurately control the potential of a working electrode with respect to a reference electrode by forcing the necessary current through an auxiliary electrode. This current also passes through the working electrode and is measured using any known current to voltage transducer. Sometimes the control potential, also called the applied potential, is varied over time according to a predetermined program, for example to analyze multiple species in the sample.

Liquid mercury as an electrode material in electrochemical research is widely accepted because of its good physical and electrical characteristics. It has a wide liquid temperature range (−38.9° TO 356.9° C.) and electrodes of various shapes can be easily prepared. In contrast to solid electrode materials, the active surface of such electrodes is highly uniform and easily reproducible if the mercury is clean. Most importantly, mercury also has a very high overvoltage for hydrogen evolution relative to other metallic and carbon electrodes so that electrochemical reactions that require more negative potentials can be carried out without as much background interference.

Several types of apparatus utilizing liquid mercury electrodes have been developed since their invention circa 1922 to help simplify or improve electrochemical investigations. Among those which are well known to those skilled in this art are: dropping mercury electrodes (DME), hanging mercury drop electrodes (HMDE), static mercury drop electrodes (SMDE), streaming mercury electrodes (SME), mercury film electrodes (MFE), and, more recently, controlled growth mercury electrodes (CGME). See, for example, U.S. Pat. No. 4,548,679 (Guidelli et al) which discloses apparatus for the automatic control of the growth or size of a hanging mercury drop; U.S. Pat. No. 4,661,210 (Tenygl) which discloses methods and apparatus for electrochemical analysis of solutions by voltammetry using a pulsating liquid mercury electrode and solution within a small volume capillary tube; U.S. Pat. No. 4,846,955 (Osteryoung et at) which also relates to the control of growth or size of a mercury drop electrode; U.S. Pat. No. 5,131,999 (Gunasingham) discloses a flow cell using a renewable mercury electrode; U.S. Pat. No. 5,292,423 (Wang) which relates to methods and apparatus for trace metal testing using mercury coated, screen-printed flat film electrodes; U.S. Pat. No. 5,326,451 (Ekechukwu) which discloses a liquid dropping electrode not made of mercury for use in non-polar solutions; and U.S. Pat. No. 5,378,343 (Kounaves et al) also disclosing mercury coated flat film electrodes.

However, these prior art devices have a number of disadvantages when used to determine trace amounts of analytes, drugs or poisons, in samples of complex biological fluids, such as blood, urine, tissue homogenates, or in environmental samples.

One application of increasing importance is the determination of heavy metals (e.g. lead) in biological samples (e.g. blood). Currently, the most widely used analytical techniques are atomic absorption and inductively coupled plasma spectroscopy but, due to the advanced nature of these methods, highly trained personnel and expensive equipment is required. Scientists would like to use anodic stripping voltammetry for this purpose wherein the metal ions present in the sample would be electroplated onto a mercury electrode and subsequently removed (stripped) electrochemically. The current recorded during stripping is proportional to the concentration of the metal of interest. This method would be highly sensitive to many metal ions and could be operated at much lower cost than the commonly used methods. Potentiometric Stripping Analysis is another variation on this same theme which would be useful with improved electrodes.

Although Mercury Drop Electrodes provide a means for continuously renewing the electrode surface by releasing a used drop and forming a new one, it is still directly in contact with the sample media and hence electrode contamination or fouling from common biological components in the sample is a significant problem. Also, all mercury drop techniques introduce used mercury drops into the sample container during the analysis which contaminates the sample and makes recovery of the mercury, for proper disposal as a health hazard, or further use of the sample, which may be quite precious, difficult at best. Apart from this, currently available designs of mercury drop electrodes do not allow use of very small, microliter, volume samples which are usually the amounts available in biological research.

Routine use of a mercury electrode could be substantially increased if one could be incorporated into a flow cell arrangement, i.e. to analyze a flowing stream of analyte solution, such as in liquid chromatographic detection of reducible organic compounds. However, the stability of a mercury drop in a flow cell is greatly reduced and consequently the background electrical noise in the analytical signal is so high that the accurately processing of the data is jeopardized. The detection limit achievable in a particular analysis under these conditions is unavoidably high and hence the quality of analytical data becomes unsatisfactory.

Mercury Film Electrodes can, on the other hand, be easily incorporated into a flow cell but their stability, and therefore data reproducibility, is dependent on the adhesion of the mercury film to the substrate material. In addition, MFEs on different substrates perform differently based on the substrate surface characteristics, thereby questioning the integrity of the analysis. Metallic substrates provide better adhesion than carbon surfaces but the solubility of the solid surface in the mercury discourages long term use. For example, mercury plated onto a gold surface will slowly dissolve the gold so that after a time, the active electrode surface becomes a gold/mercury amalgam with different electrical characteristics. The useful lifetime of a film electrode depends on the type of base metal, the amount of mercury plated and its operating conditions. In the case of a carbon base surface, there is no alloying interaction that changes the nature of the mercury but the porosity of the surface affects some applications and the cleaning of the surface or recovery of metals deposited on the electrode during anodic stripping voltammetry can be difficult if not impossible. Further, mercury films, especially on carbon substrates, which are subject to flowing streams of analyte can change surface area continuously, due to loss of mercury, thereby degrading the confidence and reproducibility of the analytical data.

Mercury Film Electrodes have been coated with various polymeric materials in order to try to circumvent the fouling problems by partially filtering the unwanted electroactive and surface active species but the reproduction of a particular coating thickness, which is necessary to maintain a constant performance level from time to time, is inherently very difficult.

It is therefore a general object of the present invention to provide a new and improved method and apparatus for forming a liquid mercury electrode and in particular an electrode having a small, renewable active analyzing surface, which is protected from fouling, usable in stationary or flowing analytical solutions and without contaminating such solutions with used mercury.

SUMMARY OF THE INVENTION

The present invention aims to overcome some of the disadvantages of the prior art as well as offer certain other advantages by teaching a novel method of making and using a mercury electrode assembly having a renewable analyzing surface resistant to contamination or fouling. Basically, the assembly comprises a cylindrical liquid mercury thread, preferably of micrometer diameter and of any desired length, which is delivered to and movable through a short fixed length of thin walled tubular semipermeable membrane so that the electrode's active (analyzing) surface is protected from fouling or contamination and can be easily renewed whenever desired by advancing the mercury thread through the tubular membrane. The active surface can be inserted into stationary or flowing electrochemical cells and used as the working electrode, along with reference and auxiliary electrodes, for analysis of solutions of interest or may be even inserted directly into a living organism for real time determination of both the presence and quantity of analytes constituted in complex biological fluids in vivo.

In the present invention, semipermeable membrane means any material which is permeable to the ions of interest but not significantly permeable to larger contaminates, such as proteins, or other organic molecules, and, of course, the liquid mercury. Several suitable polymeric films are known in the art and widely used for other purposes, such as hydrophilic dialysis. One example used in the apparatus described below is regenerated cellulose.

BRIEF DESCRIPTION OF THE DRAWINGS

While this specification concludes with claims particularly pointing out and the subject matter which is now regarded as the invention, it is believed that the broader aspects of the invention, as well as several of the features and advantages thereof, may be better understood by reference to the following detailed description of a presently preferred embodiment of the invention when taken in connection with the accompanying drawings in which:

DETAILED DESCRIPTION OF THE INVENTION

Figure 1:
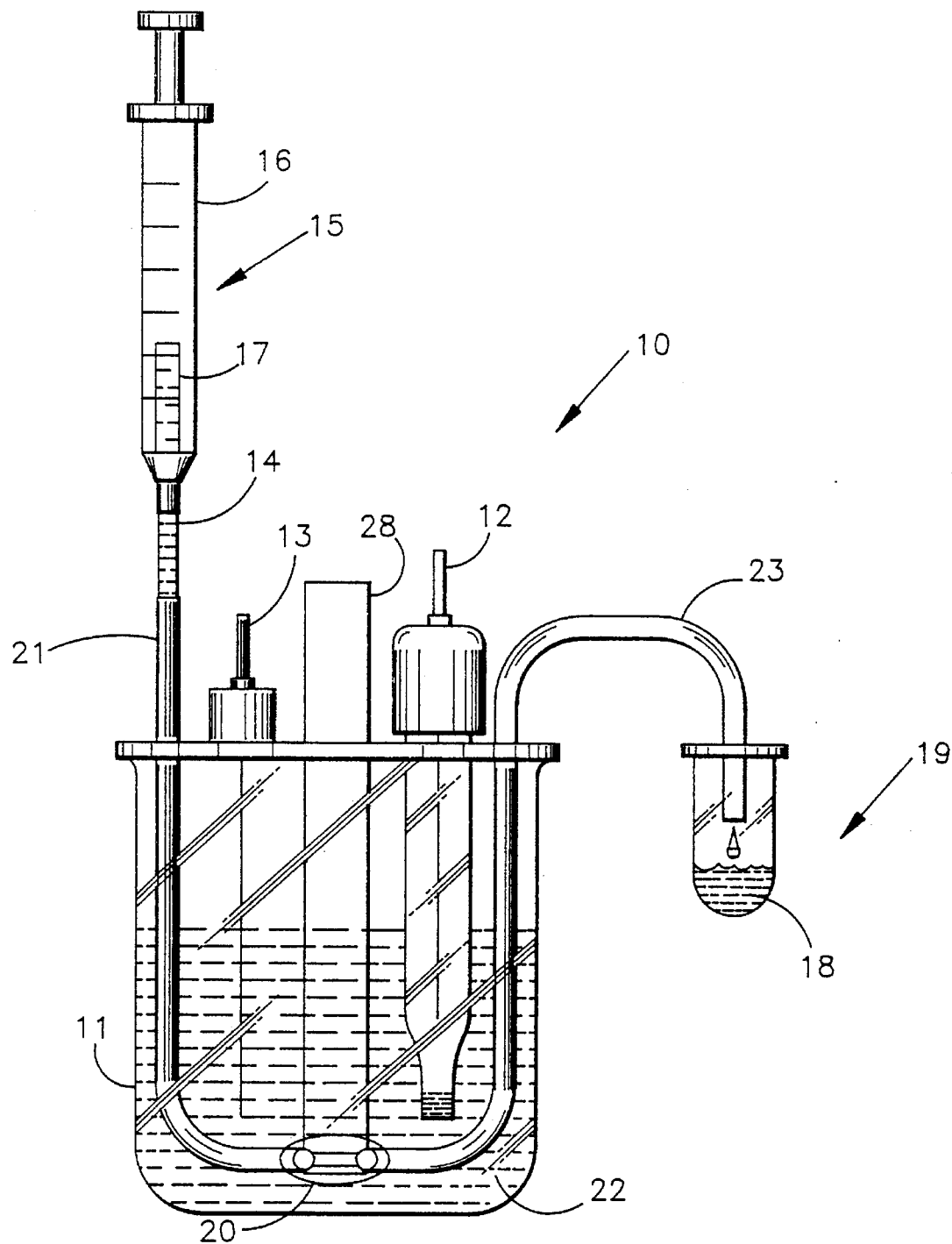
FIG. 1 illustrates the arrangement of apparatus in a simple electrochemical cell having a dip type mercury thread working electrode embodying the present invention.

Referring now to the drawings and particularly to FIG. 1, there is shown one embodiment of the present invention in which a simple electrochemical cell (10) is formed by a liquid container (11), in this case a glass beaker, to hold the solution (22) to be analyzed and three electrodes; a Ag/AgCl reference electrode (12), a platinum wire auxiliary electrode (13) and a working electrode assembly (15). Since the construction of, and ancillary electrical circuitry for using, reference electrodes and auxiliary electrodes are well known in the art, they will not be discussed in detail here.

The working electrode assembly (15) consists of a means for supplying a movable thread of fresh mercury (17), which in this case is a plastic syringe (16) but could be any type of reservoir and pump, a means for providing an electrical connection to the mercury thread, here a metal needle (14) in the syringe (16), a length of inert tubing (21) connected to the needle (14) to convey the mercury into the container and to the active surface region (20), described later, and then out of the cell (10) through a length of exit tubing (23). Used mercury (18) may be collected in a reservoir (19) for recycling. Preferably, a syringe pump (not shown), well known in the art, is used to move the syringe and advance the mercury since it may be accurately controlled by a digital stepping motor in an automated analysis system.

Figure 2:
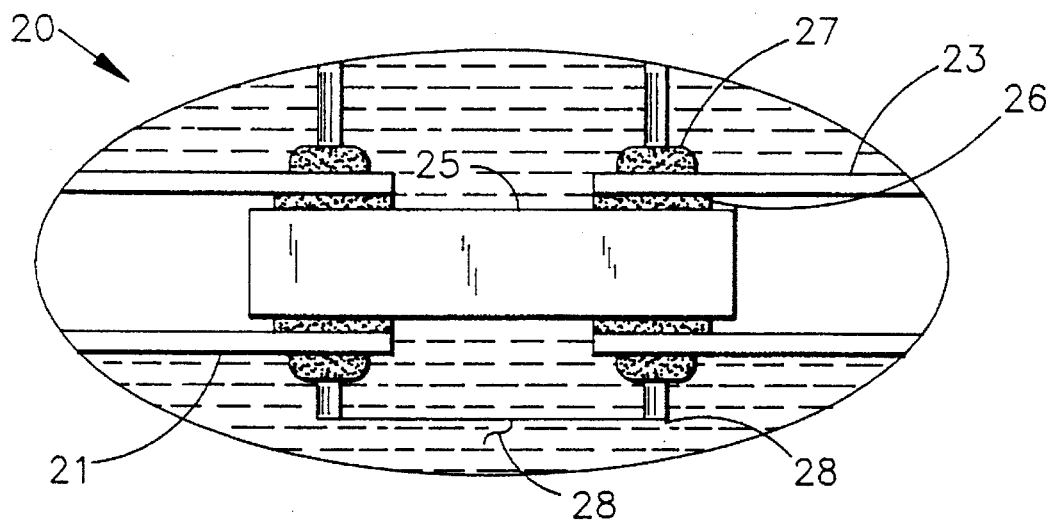
FIG. 2 is an enlarged cross sectional view of the working electrode's active surface region in the apparatus of FIG. 1.

The active surface region (20) of the working electrode assembly (15), shown more clearly in FIG. 2, is formed by a short, fixed length of thin walled tubular semipermeable membrane (25) fixed between the inlet tube (21) and the outlet tube (23). The membrane (25) is firmly attached and sealed to the tubing (21, 23) by glue or cement (26). Preferably, the tubing is also glued (27) to a support (28), in this case a plastic tube, in order to provide some protection and rigidity to the joints. In use, the liquid mercury thread within the semi-permeable membrane (25) will function as the working electrode's active surface and any electroactive species in the solution (22) which is small enough to diffuse through the membrane's "micropores" can be analyzed. Whenever the active surface becomes fouled or contaminated, the mercury thread can be advanced through the membrane, thus renewing the active surface with fresh mercury.

Figure 3:
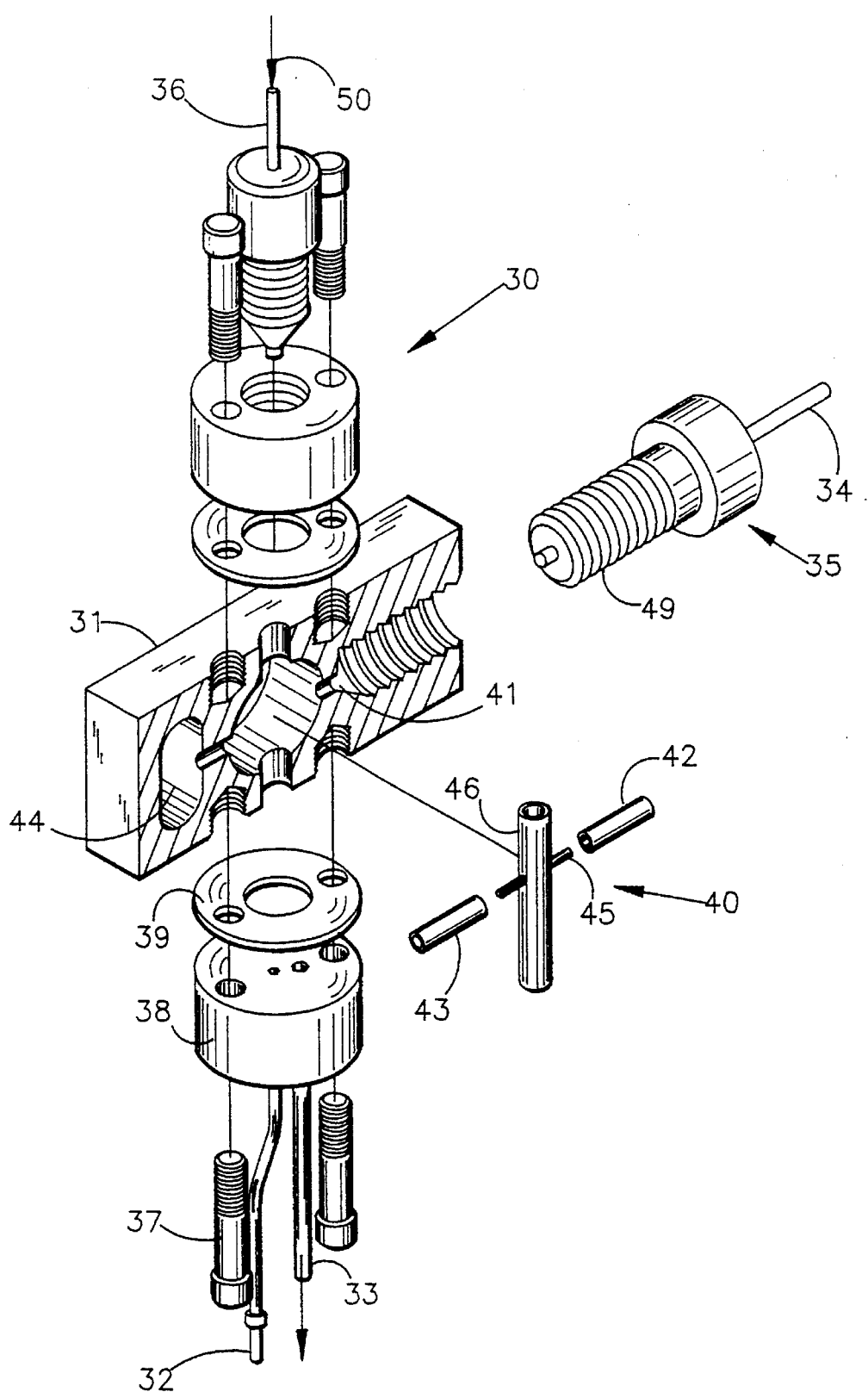
FIG. 3 illustrates the arrangement of a mercury thread electrode embodying the present invention in a typical flow cell apparatus.

Turning now to FIG. 3, there is illustrated an exploded view of one example of a flowcell assembly (30), for analyzing a flowing stream of liquid (50), which includes a body (31), preferably made of a non-conductive plastic, a working electrode (35), described below, a reference electrode (32), comprising a AgCl coated silver disk on the end of a wire exiting the body, an auxiliary electrode (33), comprising a stainless steel tube which also serves to drain the flowing liquid from the body, and various bolts (37), connectors or spacers (38) and gaskets (39) for positioning the electrodes and holding the assembly together. Again, since the construction of, and ancillary electrical circuitry for using, reference electrodes and auxiliary electrodes are generally well known in the art, they will not be discussed in detail here.

The working electrode (35) comprises a chamber (41) in the body (31) for holding a small supply of fresh mercury, a threaded plug (49) for forcing mercury from the chamber as it is turned, and a metallic pin (34) for electrical connection to the mercury within the chamber. The mercury supply chamber (41) is in fluid communication with a short length of plastic tubing (42) which itself is connected to the input end of a tubular, semipermeable membrane (45) to form the active surface region (40), described below, of the working electrode. The output end of the tubular membrane (45) is connected to another short length of tubing (43) for conveying used mercury to a collection reservoir, which may be either a chamber (44) within the body (31) as illustrated in FIG. 3 or a container outside the cell, as was shown in FIG. 1.

Alternately, the working electrode (35) may comprise a somewhat simpler means for supplying a thread of mercury similar to that shown in FIG. 1, i.e. a remote syringe pump containing fresh mercury in communication with the membrane (45) via a longer length of plastic tubing (42) thereby eliminating the threaded plug (49) and internal mercury supply chamber. Such an arrangement has the advantage of easily being automated.

In use, a flowing stream of liquid (50) to be analyzed is introduced into the cell body (31) through inlet conduit (36) and flows to and through a central section of conduit (46) in which the tubular semipermeable membrane (45) which forms the working electrode's active surface region has been inserted, here transversely, into the liquid flow. A small diameter thread of liquid mercury is introduced into the tubular membrane (45) by rotating the threaded plug (49) into the body (31) to push mercury from the supply chamber (41) through the inlet tube (42). Mercury within the membrane, as well as the reference electrode (32) and the auxiliary electrode (33), is in electrical communication with the liquid (50) flowing in conduit (46) so that it may be analyzed. The metal tube (33), which serves as the auxiliary electrode, receives the liquid flow from the central section of the conduit and directs it out of the flowcell.

Figure 4:
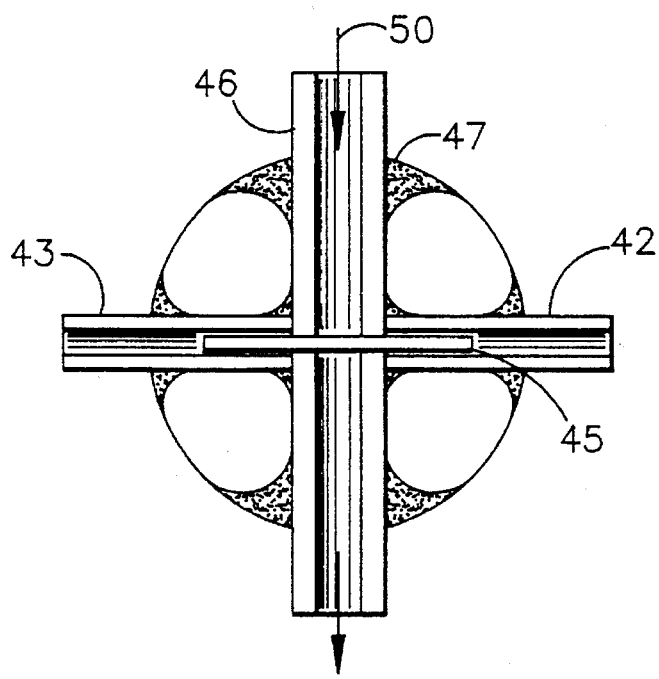
FIG. 4 is an enlarged cross sectional view of the active electrode surface region of the apparatus of FIG. 3.

As better shown in FIG. 4, the active surface region (40) of the working electrode (35) is formed by the portion of the membrane (45) which extends through the conduit (46) carrying the flow (50) of liquid to be analyzed. Preferably, the tubes and conduits are held in place in the body by glue or cement (47). When a thread of mercury is advanced from the source through the membrane (45) and is properly charged, the type and amount of electroactive species in the liquid stream (50) which diffuse through the membrane's micropores can be analyzed. If the active surface becomes contaminated, it may be easily renewed by further advancing fresh mercury from the supply chamber (41) into and through the membrane. Or, in the alternate embodiment, fresh mercury may be supplied from a syringe pump to advance the thread through the membrane.

While the present invention has been described in terms more or less specific to one preferred embodiment, it is expected that various alterations, modifications, or permutations thereof will be readily apparent to those skilled in the art. Therefore, it should be understood that the invention is not to be limited to the specific features shown or described, but it is intended that all equivalents be embraced within the spirit and scope of the invention as defined by the appended claims.

What is claimed is:

1. An improved liquid mercury electrode for electrochemical analysis of liquid solutions comprising a elongated thread of liquid mercury contained within an inert tube which, at one point along its length, includes a section of semipermeable membrane surrounding and forming the electrode's active surface wherein the mercury thread is capable of being advanced in the tube to expose a fresh active surface.

2. The mercury electrode of claim 1 further including a means for supplying a movable thread of fresh mercury and means for providing an electrical connection to the mercury thread.

3. The electrode of claim 2 wherein the means for supplying a movable thread of mercury includes a pump in communication with a reservoir of mercury.

4. The electrode of claim 2 wherein the means for supplying a movable thread of mercury includes a syringe containing mercury and the means for providing an electrical connection to the mercury thread is a metallic needle in the syringe.

5. An electrochemical cell for analyzing a liquid solution having a container means for holding solution to be analyzed; a reference electrode, an auxiliary electrode and a working electrode, wherein the working electrode comprises a source means for supplying a movable thread of liquid mercury, a means for providing an electrical connection to the mercury thread, and a length of inert tubing connected to the source to convey the mercury thread into the container to an active surface region, said active surface region formed by a length of tubular semipermeable membrane which surrounds a portion of the mercury thread within the cell.

6. The electrochemical cell of claim 5 wherein the means for supplying a movable thread of mercury includes a syringe containing mercury and the means for providing an electrical connection to the mercury thread is a metallic needle in the syringe.

7. The electrochemical cell of claim 5 wherein the means for supplying a movable thread of mercury includes a pump in communication with a reservoir of liquid mercury.

8. An electrochemical flowcell for analyzing a flowing stream of liquid comprising a conduit means for directing the liquid to be analyzed through the flowcell; a reference electrode, an auxiliary electrode and a working electrode, all in electrical communication with the liquid in the conduit, wherein the working electrode comprises a source means for supplying a movable thread of liquid mercury, a means for providing an electrical connection to the mercury thread, a length of inert tubing connected to the source to convey the mercury thread into the flowcell to an active surface region, said active surface region formed by a length of tubular semipermeable membrane, inserted through the conduit and into the flowing stream of liquid, which surrounds a portion of the mercury thread.

9. The flowcell of claim 8 wherein the means for supplying a movable thread of mercury includes a syringe containing mercury and the means for providing an electrical connection to the mercury thread is a metallic needle in the syringe.

10. The flowcell of claim 8 wherein the means for supplying a movable thread of mercury includes a pump in communication with a reservoir of liquid mercury.

* * * * *